(12) United States Patent
Jakob et al.

(10) Patent No.: US 8,716,519 B2
(45) Date of Patent: May 6, 2014

(54) CROSS-LINKABLE MONOMERS AND POLYMERS AND THE USE THEREOF

(75) Inventors: Martin Jakob, Kelkheim (DE); Stefan Nogai, Heidelberg (DE)

(73) Assignee: Celanese Emulsions GmbH, Kronberg/Ts. (DE)

( * ) Notice: Subject to any disclaimer, the term of this patent is extended or adjusted under 35 U.S.C. 154(b) by 702 days.

(21) Appl. No.: 12/674,247

(22) PCT Filed: Jul. 11, 2008

(86) PCT No.: PCT/EP2008/005686
§ 371 (c)(1),
(2), (4) Date: Mar. 24, 2011

(87) PCT Pub. No.: WO2009/024216
PCT Pub. Date: Feb. 26, 2009

(65) Prior Publication Data
US 2011/0190462 A1    Aug. 4, 2011

(30) Foreign Application Priority Data

Aug. 20, 2007  (DE) .......................... 10 2007 039 312

(51) Int. Cl.
*C07C 309/21* (2006.01)
*C07C 309/22* (2006.01)

(52) U.S. Cl.
USPC ........... 562/111; 562/109; 562/110; 568/458; 568/31; 526/287

(58) Field of Classification Search
USPC ........... 526/287; 568/458, 287; 562/109, 110, 562/111
See application file for complete search history.

(56) References Cited

U.S. PATENT DOCUMENTS

| | | | |
|---|---|---|---|
| 3,579,565 A * | 5/1971 | Zaslowsky ..................... | 560/195 |
| 4,118,357 A | 10/1978 | Brabetz et al. | |
| 4,242,281 A * | 12/1980 | Sprecker et al. ............. | 568/458 |
| 4,250,070 A | 2/1981 | Ley et al. | |
| 4,404,185 A * | 9/1983 | Maccone et al. ................ | 424/84 |
| 5,021,529 A | 6/1991 | Garrett | |
| 5,258,477 A | 11/1993 | Tsai et al. | |
| 5,296,532 A | 3/1994 | Haerzschel et al. | |
| 5,401,582 A | 3/1995 | Weyland et al. | |
| 5,545,684 A | 8/1996 | Jakob et al. | |
| 5,847,201 A * | 12/1998 | Wieczorek ...................... | 562/43 |
| 7,022,461 B2 * | 4/2006 | Zheng et al. ................ | 430/278.1 |
| 7,312,272 B2 | 12/2007 | Jakob et al. | |
| 7,585,915 B2 | 9/2009 | Jakob et al. | |

FOREIGN PATENT DOCUMENTS

| | | |
|---|---|---|
| DE | 2058773 A1 | 5/1972 |
| DE | 2261402 | 7/1974 |
| DE | 2620738 | 12/1977 |
| DE | 3942628 | 6/1991 |
| DE | 4003422 | 8/1991 |
| EP | 0003516 | 8/1979 |
| EP | 0514654 | 11/1992 |
| EP | 0686682 | 12/1995 |
| EP | 1505085 | 2/2005 |
| EP | 1458774 | 6/2006 |
| GB | 1322971 A | 7/1972 |
| GB | 1440337 | 6/1976 |
| JP | 6072954 | 3/1994 |
| WO | 98/54237 | 12/1998 |

OTHER PUBLICATIONS

K. Hübner and F. Kollinsky, Angew. Makromol. Chem. 11, 125-134 (1970) (For English description, reference contains an English Abstract. See also, specification, p. 1, line 18—p. 2, line 6.).
Zabranski et al. in Makromol. Chem. 186, 215-222 (1985).
Luan et al. in Zhongguo Pige (China Leather) 32, 24-28 (2003) (For English description, reference contains an English Abstract. See also, specification, p. 14, line 28—p. 15, line 9.).
P.L. Anelli, F. Montanari and S. Quici in Organic Syntheses, Coll. vol. 8, 367 (1993); vol. 69, 212 (1990).

(Continued)

*Primary Examiner* — Ling Choi
*Assistant Examiner* — David L Miller
(74) *Attorney, Agent, or Firm* — Dority & Manning, P.A.

(57) ABSTRACT

The invention relates to novel cross-linkable monomers that may be polymerized with ethylenically unsaturated comonomers to form cross-linkable copolymers. Said copolymers may particularly be used in the form of aqueous dispersions as formaldehyde-free adhesives or as coatings with good water resistance. The cross-linkable monomer is a compound in acid or salt form comprising an anion of the formula (I) and one or more cations for producing electrical neutrality, where $R^1$ and $R^2$ represent, independently of one another, hydrogen alkyl, cycloalkyl, aryl, aralkyl, $—COOR^5$, $—COO^-$ $cat^+$ or $—CON(R^6R^7)$, $R^6$ and $R^7$ represent, independently of one another, hydrogen, alkyl, or aryl, $cat^+$ represents a monovalent cation, and one of the groups $R^1$ or $R^2$ may also represent a group $—X—R^4—CR^5(OH)SO_3^-$), wherein X, $R^4$, and $R^5$ assume one of the meanings listed below, $R^3$ represents hydrogen, alkyl, or aryl, X is selected from the group of direct C—C bond, —O—, $—CH_2—O—$, $—CH_2—NR^8—$, —COO— or $—CONR^8—$, $R^8$ represents hydrogen, alkyl, or aryl, $R^4$ represents alkylene, polyoxyalkylene, cycloalkylene, or arylene, and $R^5$ represents hydrogen, alkyl, cycloalkyl, or aryl.

(I)

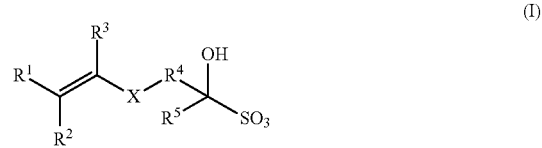

14 Claims, No Drawings

(56) References Cited

OTHER PUBLICATIONS

Houben-Weyl, Methoden der organischen Chemi [Methods of Organic Chemistry], vol. VII/I, Sauerstoffverbindungen [Oxygen Compounds] II, Georg-Thieme-Verlag, Stuttgart 1954, pp. 482-487. (For English description, see specification, p. 15, line 20—p. 16, line 14.).

Houben-Weyl, Methoden der organischen Chemi [Methods of Organic Chemistry], vol. XIV/1, Makromolekulare Stoff [Macromolecular Compounds, Georg-Thieme-Verlag, Stuttgart 1961, pp. 411-420 (For English description, see specification, p. 26, line 25—p. 27, line 28.).

Houben-Weyl, Methoden der organischen Chemi [Methods of Organic Chemistry], vol. XIV/I, Makromolekulare Staff [Macromolecular Compounds, Georg-Thieme-Verlag, Stuttgart 1961, pp. 192-208 (For English description, see specification, p. 28, lines 10-17.).

D. Diederich, Chemie in unserer Zeit 1990, 24, pp. 135-142, Verlag Chemie, Weinheim (For English description, see specification, p. 31, line 34—p. 32, line 24.).

International Report on Patentability for PCT/EP2008/005686, issued on Feb. 24, 2010.

Search Report for PCT/EP2008/005686 dated Dec. 3, 2008, 4 pages.

* cited by examiner

CROSS-LINKABLE MONOMERS AND POLYMERS AND THE USE THEREOF

The present invention relates to crosslinkable monomers and copolymers derived therefrom, in particular in the form of aqueous polymer dispersions. Films comprising these copolymers are distinguished by good water resistance and are formaldehyde-free. The invention furthermore relates to the use of these monomers and copolymers, for example for the adhesive bonding of substrates of all types.

Aqueous polymer dispersions, including those based on polyvinyl esters, such as homopolymeric polyvinyl acetate, or copolymers of vinyl acetate and ethylene, are widely used industrially as adhesives, coating materials or binders. These polymers may suffer a considerable loss in cohesion after exposure to water or to solvents, which can be reduced by addition of crosslinking monomers incorporated in the form of polymerized units or externally added compounds, such as selected urea-, melamine-, phenol- or glyoxal-based resins. A customary crosslinking monomer is N-methylol-acrylamide ("NMA" below). The N-methylol group of the NMA (or also N-methylolmethacrylamide) can subsequently self-crosslink and thus improve the film cohesion, but also permit, via amidomethylation, in particular of hydroxyl groups, covalent bonding of the emulsion polymer to hydroxy-functional stabilizers, such as to cellulose ethers or to polyvinyl alcohol or to substrate surfaces, such as to textiles, wood or paper. However, the industrial commercial form of this product may contain up to 2% by weight of free formaldehyde, which is introduced into the dispersions. Formaldehyde is also released during the crosslinking reaction itself—depending on the conditions chosen. Possible mechanisms for this are described in the literature, for example by K. Hübner and F. Kollinsky, Angew. Makromol. Chem. 11, 125-134 (1970).

Formaldehyde is a hazardous substance with an irritant and sensitizing effect. Moreover, it has for some time also been considered to have a carcinogenic potential. In the past, many attempts have therefore been made to develop functional crosslinkable monomers having a similar potential, such as N-methylolacrylamide or N-methylolmethacrylamide, and to use said monomers as a functional component in polymer dispersions.

Etherified N-methylol monomers, such N-methoxy-methyl(meth)acrylamide, N-butoxymethyl(meth)acrylamide and N-isobutoxymethyl(meth)acrylamide, have long been known. However, these do not have the required reactivities for many applications, in particular not in the case of applications where the crosslinking has to take place as low as at room temperature. Accordingly, the products are not a substitute for many applications.

U.S. Pat. No. 5,021,529 describes formaldehyde-free interpolymers suitable for the production of impregnated or treated papers, textile and nonwovens. Crosslinking monomers proposed are N-ethylol(meth)acrylamide and -maleimide, N-propylol(meth)acrylamide, N-butylol-(meth)acrylamide and -maleimide and N-benzylol-(meth)acrylamide. Temperature ranges from 120° C. to 160° C. are suitable for curing, for example in the finishing of textile fabrics.

EP-A-514,654 describes formaldehyde-free crosslinking emulsion polymers derived from N-(2,2-dialkoxy-1-hydroxy)ethylacrylamide and vinyl esters. The dispersions thus obtained are suitable as binders for nonwovens or fiberfill and as wood adhesives. The reactivity of this system corresponds to that of a polymer crosslinked via N-methylolacrylamide. In the case of the gluing of wood, a sufficient reactivity is achieved after thermal activation in the case of hot adhesive bonding. This is described in example 18 of the document.

Aldehyde-functional monomers have been known in principle for a relatively long time. EP-A-003,516 proposes, for example, (meth)acryloxyalkylpropanals as crosslinking agents. These are obtained easily by esterification of β-hydroxyalkylpropanals. These carbonyl-functional monomers can be crosslinked with polyhydrazines with hydrazide formation. However, U.S. Pat. No. 5,258,477 discloses that the free aldehyde group of such monomers tends toward chain transfer during the polymerization and precrosslinks the polymers in this manner. As a result, some of the reactive groups are no longer available for the end application.

In U.S. Pat. No. 5,258,477, this technical disadvantage is overcome by masking the aldehyde monomers as acetal. Here, numerous structures based on crotonic, maleic, fumaric or itaconic acid esterified with 2,2-dimethyl-3-hydroxypropanal are proposed. These esters are reacted with mono- or difunctional alcohols to give open or cyclic acetals. Emulsion polymers with these acetal monomers are suitable as binders for nonwovens.

For improving the wet strength of paper, acetal monomers based on (meth)acrylate or (meth)acrylamide are used together with selected cationic monomers in WO-A-98/54,237. The acetals N-(2,2-dimethoxyethyl)-N-methylacrylamide and 3,3-dimethoxy-1-methylethyl acrylate may be mentioned by way of example.

Emulsion polymers based on vinyl esters, in particular vinyl acetate, are usually rendered slightly acidic. In this environment, the acetals undergo a slow irreversible hydrolysis with liberation of the reactive aldehydes. If functional groups which can react with the aldehydes are present in the dispersion, for example when polyvinyl alcohol is used as protective colloid, this leads to an undesirable reduction in the storage stability. The alcohols liberated during the hydrolysis of the acetals increase the content of VOC (volatile organic compounds), which is undesired in some applications.

There is therefore still a need on the market for functional comonomers which are suitable for the preparation of crosslinkable polymers which effectively crosslink, in particular from emulsion, without liberation of formaldehyde, without having the disadvantages of the systems of the prior art.

Accordingly, it is the object of this invention to provide crosslinking monomers and copolymers derived therefrom which permit effective crosslinking in addition to excellent storage stability and which are not formaldehyde sources.

A further object of the present invention consists in the provision of crosslinking monomers and copolymers derived therefrom which crosslink at room temperature and which are capable of reacting with hydroxy-functional groups. These groups may be, for example, groups of constituents of a formulation, for example of an emulsion polymer, such as groups in stabilizers, or they may be groups in substrates, for example those in cellulosic substrates, such as textiles, paper and wood.

Yet a further object of the present invention consists in the provision of crosslinking monomers and copolymers derived therefrom which are readily obtainable.

These objects are achieved by the monomers and copolymers described below.

The invention relates to copolymers derived from at least one monomer in acid or salt form, which contains an anion of the formula I and one or more cations for producing electroneutrality, and at least one further monomer which can undergo free radical copolymerization therewith

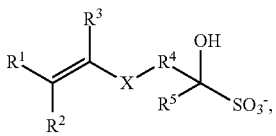
(I)

in which

R[1] and R[2], independently of one another, are hydrogen, alkyl, cycloalkyl, aryl, aralkyl, —COOR[5], —COO⁻ Cat⁺ or —CON(R[6]R[7]), R[6] and R[7], independently of one another, are hydrogen, alkyl or aryl, Cat⁺ is a monovalent cation and one of the radicals R[1] or R[2] may also be an —X—R[4]—CR[5](OH)(SO$_3^-$) group, X, R[4] and R[5] assuming one of the meanings stated below, R[3] is hydrogen, alkyl or aryl and X is selected from the group consisting of a direct C—C bond, —O—, —CH$_2$—O—, —CH$_2$—NR[8]—, —COO— or —CONR[8]—, R[8] is hydrogen, alkyl or aryl, R[4] is alkylene, polyoxyalkylene, cycloalkylene or arylene and R[5] is hydrogen, alkyl, cycloalkyl or aryl.

The invention also relates to compounds in acid or salt form which contain an anion of the formula (I) and one or more cations for producing electroneutrality.

These compounds are distinguished by high stability and can be isolated as a solid substance. The corresponding precursor substances, for example the aldehydes, are frequently present in liquid form and in some cases are chemically labile.

If groups or substituents can occur several times in the compounds of the formula (I), they can, independently of one another, have the stated meanings and can in each case be identical or different.

The anions and cations of the compounds of the formula (I) should be chosen so that an electrically neutral compound forms.

The cations for producing electroneutrality are as a rule mono- to tetravalent cations, preferably hydrogen, ammonium or mono- to tetravalent metal ions.

If any groups are alkyl, they may be straight-chain or branched. This is also true if they are present in other groups, for example in alkoxy groups, alkoxycarbonyl groups or in amino groups, or if they are substituted. Alkyl radicals usually contain one to eighteen carbon atoms, preferably one to ten carbon atoms, in particular one to eight carbon atoms. Alkyl radicals may in turn be substituted, for example by cycloalkyl, alkoxy or aryl radicals and/or by halogen. Unsubstituted alkyl radicals are preferred.

Examples of alkyl groups are methyl, ethyl, n-propyl, n-butyl, n-pentyl, n-hexyl, n-heptyl, n-octyl, n-nonyl, n-decyl, nidodecyl, n-lauryl, n-hexadecyl, n-octadecyl, isopropyl, isobutyl, isopentyl, sec-butyl, tert-butyl, neopentyl, 3,3-dimethylbutyl or 2-ethylhexyl.

If any groups are cycloalkyl, they are saturated monocyclic or polycyclic hydrocarbon radicals. Monocyclic cycloalkyl radicals containing five to eight ring carbon atoms, preferably five or six ring carbon atoms, are preferred. Cycloalkyl radicals may in turn be substituted, for example by alkyl, alkoxy or aryl radicals and/or by halogen. Unsubstituted cycloalkyl radicals are preferred.

Examples of cycloalkyl radicals are cyclopentyl, cyclohexyl, cycloheptyl and cyclooctyl, which, for example, may be substituted by one or more identical or different ($C_1$-$C_4$)-alkyl radicals, in particular by methyl.

If any groups are aryl, they are carbocyclic or heterocyclic aromatic radicals, preferably phenyl, naphthyl or heteroaryl. Aryl radicals may be unsubstituted or mono- or polysubstituted. Examples of substituents are alkyl, alkoxy, hydroxyl, amino, carboxyl and/or carboxylic ester groups and halogen. Alkyl-substituted or in particular unsubstituted aryl radicals are preferred. Phenyl is very particularly preferred.

Heterocyclic aromatic radicals are preferably 5- to 7-membered unsaturated heterocycles which have one or more heteroatoms from the series consisting of O, N and S. The radicals derived from these heterocycles may be bonded via any ring carbon atom.

If any groups are aralkyl, they are aryl radicals which are linked to the corresponding radical via an alkylene group. A preferred example of an aralkyl radical is benzyl. Aralkyl radicals may be unsubstituted or mono- or polysubstituted. Examples of substituents are mentioned in the description of the aryl radicals. Unsubstituted aralkyl radicals are preferred.

Halogen is fluorine, chlorine, bromine or iodine, preferably chlorine.

If any groups are alkylene, they may be straight-chain or branched. Alkylene radicals are divalent aliphatic hydrocarbon radicals. They usually contain one to eighteen carbon atoms, preferably one to six carbon atoms. Alkylene radicals may in turn be substituted, for example by cycloalkyl, alkoxy, hydroxyl or aryl radicals and/or by halogen. Unsubstituted alkylene radicals are preferred.

Examples of alkylene groups are radicals of the general formula (II)

in which m is an integer from 1 to 18, in particular from 1 to 8, very particularly preferably from 1 to 6.

Very particularly preferred alkylene radicals are radicals of the formulae —CH$_2$—, —CH$_2$—CH$_2$—, —CH(CH$_3$)—CH$_2$—, —(CH$_2$)$_3$— and —(CH$_2$)$_4$—.

If any groups are polyoxyalkylene, they may be straight-chain or branched. Polyoxyalkylene radicals are divalent aliphatic polyether radicals. The repeating hydrocarbon units of these polyether radicals usually contain two to six carbon atoms, preferably two to four carbon atoms. Polyoxyalkylene radicals may in turn be substituted, for example by cycloalkyl, alkoxy or aryl radicals and/or by halogen. Unsubstituted polyoxyalkylene radicals are preferred.

Examples of polyoxyalkylene groups are radicals of the general formula (III)

in which o is an integer from 2 to 6, in particular from 2 to 4, very particularly preferably 2 or 3, and in which p is an integer from 2 to 30, in particular 2 to 10.

Very particularly preferred polyoxyalkylene radicals are unsubstituted polyoxyethylene radicals.

If any groups are cycloalkylene, they are saturated monocyclic or polycyclic divalent hydrocarbon radicals.

Monocyclic cycloalkylene radicals containing five to eight ring carbon atoms, preferably five or six ring carbon atoms, are preferred. Cycloalkylene radicals may in turn be substituted, for example by alkyl, alkoxy, hydroxyl or aryl radicals and/or by halogen. Unsubstituted cycloalkylene radicals are preferred.

Examples of cycloalkylene radicals are cyclopentylene and cyclohexylene.

If any groups are arylene, they are carbocyclic or heterocyclic divalent aromatic radicals, preferably phenylene, naphthylene or heteroarylene. Arylene radicals may be unsubstituted or mono- or polysubstituted. Examples of substituents are alkyl, alkoxy, hydroxyl, amino, carboxyl and/or carboxylic ester groups and halogen. Alkyl-substituted or in particular unsubstituted arylene radicals are preferred. Phenylene is very particularly preferred. This may be ortho-, meta- or para-phenylene.

Heterocyclic arylene radicals are preferably 5- to 7-membered unsaturated heterocycles which have one or more heteroatoms from the series consisting of O, N and S. The radicals derived from these heterocycles may be bonded via two of their ring carbon atoms.

If any radicals are monovalent cations, they may be any desired singly charged cations. Examples of preferred monovalent cations are cationic hydrogen (the proton), the ammonium cation or cations of monovalent metals, in particular of the alkali metals, such as sodium or potassium. The ammonium cation or cations of the alkali metals are preferred.

If any radicals are mono- to tetravalent cations, they may be any desired singly charged to quadruply charged cations. Examples of singly charged cations are listed in the above section. Examples of doubly charged cations are cations of divalent metals, in particular of metals of the alkaline earth metals, very particularly preferably of magnesium, of calcium or of strontium. Examples of triply charged cations are cations of trivalent metals, in particular of the metals of the third main group and subgroup of the Periodic Table of the Elements, very particularly preferably of aluminum. Examples of quadruply charged cations are cations of tetravalent metals, in particular of the metals of the fourth main group and subgroup of the Periodic Table of the Elements, very particularly preferably of tin, of zirconium and of titanium.

Compounds of the formula (I), in which $R^1$, $R^2$ and $R^3$, independently of one another, are hydrogen, alkyl, —COOR$^5$ or —COO$^-$ Cat$^+$, are preferred.

Compounds of the formula (I), in which $R^1$, $R^2$ and $R^3$, independently of one another, may be hydrogen or alkyl and one of the radicals $R^1$ or $R^2$ may be —COOR$^{5a}$ or —COO$^-$ Cat$^+$, are particularly preferred.

Compounds of the formula (I), in which $R^1$, $R^2$ and $R^3$, independently of one another, may be hydrogen or methyl and one of the radicals $R^1$ or $R^2$ may be —COOR$^{5a}$ or —COO$^-$ Cat$^+$, $R^{5a}$ being hydrogen or $C_1$-$C_6$-alkyl, are very preferred.

Likewise preferred are compounds of the formula (I), in which one of the radicals $R^1$ or $R^2$ is an —X—$R^4$—CR$^5$(OH)(SO$_3^-$) group.

Compounds of the formula (I), in which X is selected from the group consisting of —O—, —CH$_2$—O—, —CO—NR$^8$— or —COO$^-$, are preferred; —COO$^-$ is very particularly preferred.

Likewise preferred are compounds of the formula (I), in which $R^4$ is alkylene or polyoxyalkylene, particularly preferably unsubstituted $C_1$-$C_6$-alkylene and very particularly preferably unsubstituted $C_1$-$C_4$-alkylene.

Likewise preferred are compounds of the formula (I), in which $R^5$ is hydrogen or alkyl, very particularly preferably hydrogen.

Likewise preferred are compounds of the formula (I), in which n is 1 and in which M is ammonium or a monovalent metal ion.

Very particularly preferred compounds of the formula (I) are derived from acrylic acid or from methacrylic acid. These are compounds in acid or salt form which contain an anion of the formula (IVa) or of the formula (IVb) and one or more cations for producing electro-neutrality

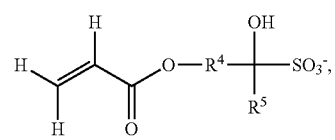

(IVa)

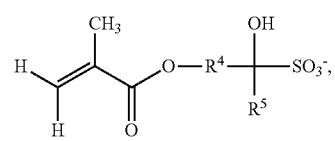

(IVb)

in which $R^4$ and $R^5$ have the meaning defined further above.

In principle, the compounds of the formula (I) are formally an addition compound of a bisulfite salt with a vinylically unsaturated carbonyl compound.

For the synthesis of the crosslinking monomers of the formula (I), the corresponding monomers having carbonyl groups, in particular having aldehyde groups ($R^5$ is H), or their acetals and optionally other masked forms are suitable as a precursor. The monomers having carbonyl groups are compounds of the formula (V)

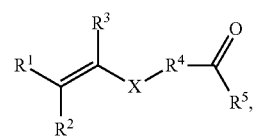

(V)

in which $R^1$, $R^2$, $R^3$, $R^4$, $R^5$ and X have the meaning defined further above.

Preferred compounds of the formula (V) where $R^4$ is —$C_3H_6$— are derived from acrylic acid or from methacrylic acid. These are compounds of the formula (V) where $R^1$, $R^2$ and $R^3$ are hydrogen and X is —CO—O— or where $R^1$ and $R^2$ are hydrogen and $R^3$ is methyl and X is —CO—O—.

In the case of the masking of the compounds of the formula (V), the protected group is removed under suitable reaction conditions before or during the preparation of the bisulfite adduct.

Preferably, free, unmasked aldehydes are used as precursors, i.e. compounds of the formula (V) in which $R^5$ is H. This synthesis of these types of compound can be carried out analogously to known processes.

Examples of the preparation of these monomers of the formula (V) are esterification of vinylically unsaturated acids with hydroxyalkanals, as described in EP-A-003,516.

These are reactions of compounds of the formula (VIa) with compounds of the formula (VIb)

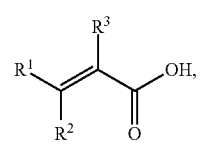

(VIa)

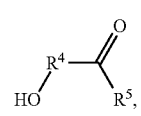

(VIb)

in which R¹, R², R⁴ and R⁵ have the meaning defined further above.

A further preparation of compounds of the formula (V) can be effected by the addition reaction of acrylic acid with acrolein to give formylethyl acrylate, as described in JP-A 06072954, example 1A.

A further preparation of compounds of the formula (V) can be effected by alkylation of salts of unsaturated carboxylic acids (VIIa) with haloacetals (VIIb), followed by the hydrolysis of the acetals obtained to give the corresponding aldehydes

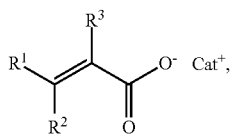

(VIIa)

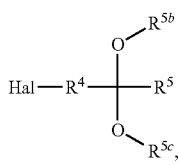

(VIIb)

in which R¹, R², R³, R⁴, R⁵ and Cat⁺ have the meaning defined further above, Hal is a halogen atom, preferably chlorine or bromine and $R^{5b}$ and $R^{5c}$, independently of one another, are alkyl radicals.

An example of such a reaction is the alkylation of salts of methacrylic acid with haloacetals, for example with 2-bromo-1,1-diethoxyethane, to give 2,2-diethoxy-ethyl methacrylate, and subsequent hydrolysis to give formylethyl methacrylate, as described by Zabranski et al. in Makromol. Chem. 186, 215-222 (1985).

A further preparation of compounds of the formula (V) can be effected by the reaction of halides of unsaturated carboxylic acids (VIIIa) with compounds of the formula (VIIIb), followed by the hydrolysis of the acetals obtained to give the corresponding aldehydes

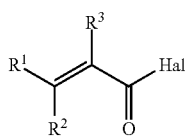

(VIIIa)

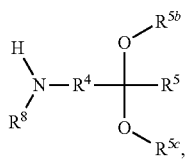

(VIIIb)

in which R¹, R², R³, R⁴, R⁵, $R^{5b}$, $R^{5c}$, R⁸ and Hal have the meaning defined further above.

An example of such a reaction is the preparation of N-(2,2-dimethoxyethyl)-N-methylmethacrylamide from N-(2,2-dimethoxyethyl)-N-methylamine and methacryloyl chloride, as described by Zabranski et al. in Makromol. Chem. 186, 224 (1985).

A further preparation of compounds of the formula (V) can be effected by oxidation of the hydroxides of the formula (IX) with pyridinium chromate

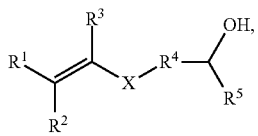

(IX)

in which R¹, R², R³, R⁴, R⁵ and X have the meaning defined further above.

An example of such a reaction is the oxidation of hydroxyalkyl(meth)acrylates with pyridinium dichromate, for example of hydroxyethyl acrylate to give formylmethyl acrylate, as described by Luan et al. in Zhongguo Pige (China Leather) 32, 24-28 (2003).

The TEMPO-catalyzed oxidation of hydroxyalkyl acrylates with hypochlorite to give formyl acrylates (e.g. 3-formylpropyl acrylate from butanediol monoacrylate, cf. example 2A) has proven particularly effective. This relatively gentle oxidation was described by P. L. Anelli, F. Montanari and S. Quici in Organic Syntheses, Coll. Vol. 8, 367 (1993); Vol. 69, 212 (1990) and leads to the desired carbonyl monomers in good yields.

The starting materials for the preparation of the compounds of the formula (V) are either known or some of them are commercially available or can be prepared by standard processes of organic chemistry.

Bisulfite adducts (also to referred to "hydrogen sulfite adducts") according to the invention can be prepared in a known manner from the precursors of the formula (V).

In principle, the preparation of these bisulfate adducts with saturated and unsaturated aldehydes is described in the literature. Reference is made to Houben-Weyl, Methoden der organischen Chemie [Methods of Organic Chemistry], Vol. VII/I, Sauerstoffverbindungen [Oxygen Compounds] II, Georg-Thieme-Verlag, Stuttgart 1954, pages 482-487.

The bisulfite adducts can be obtained by reaction with salts derived from sulfurous acid in a slightly acidic medium. Sulfites, hydrogen sulfites, disulfites or metabisulfites (pyrosulfites) of alkali metals or alkaline earth metals or of ammonium, preferably of sodium or potassium, are suitable for this purpose, or the direct reaction with sulfurous acid or by introduced sulfur dioxide is chosen. It may be necessary to establish a pH optimal for the formation of the bisulfite adducts by choosing suitable buffer systems.

It is known to work at relatively high pH values in order to avoid the competing addition reaction with the C=C double bond. In the course of this investigation, it has proven particularly expedient, for avoiding decreases in the yield due to formation of bisadducts, which can form as a result of an addition reaction with the C=C and C=O groups, to use the salt compound in a substoichiometric ratio with respect to the aldehyde used and to recover unreacted aldehyde for recycling. As a result, hydrogen sulfite undergoes addition exclusively at the more reactive carbonyl group and directs the reaction toward the target compound. Furthermore, it has proven expedient to work substantially with exclusion of oxygen in the preparation of the bisulfite adduct in order to suppress oxygen-induced redox reactions which can trigger a spontaneous polymerization. The procedure is explained in more detail in the working examples.

A particularly preferred group of the vinylically unsaturated bisulfite adducts are formylalkyl esters and -amides of aliphatic ethylenically unsaturated mono- or dicarboxylic acids, in particular of acrylic acid, of methacrylic acid, of fumaric acid, of maleic acid or of itaconic acid. These are compounds in acid or salt form which contain an anion of the formula (X) and one or more cations for producing electroneutrality

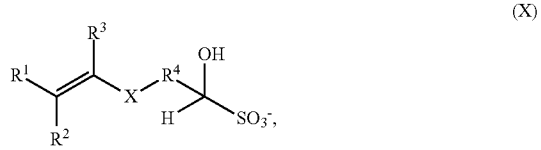

in which $R^1$, $R^2$ and $R^3$, independently of one another, are hydrogen or methyl, or $R^1$ or $R^2$ are a group of the formula —X—$R^4$—CH(OH)(SO$_3^-$), X is —CO—O— or —CO—NR$^8$—, $R^8$ is hydrogen or methyl and $R^4$ is $C_1$-$C_6$-alkylene, preferably ethylene or propylene.

The cations for producing electroneutrality are preferably mono- or divalent cations, preferably an ammonium cation, an alkali metal cation or an alkaline earth metal cation.

Particularly preferably they are bisulfite adducts of 2-formylethyl acrylate or of 3-formylpropyl acrylate. These are colorless and water-soluble solids which can be readily isolated and can be metered in in the aqueous phase during the polymerization. The salts have no defined melting point but decompose thermally at temperatures >100° C.

The spectroscopic data of both compounds are mentioned in the examples and confirm the assumed constitution.

The compounds of the formula (I) can be used as crosslinking monomers in the free radical copolymerization with ethylenically unsaturated comonomers.

The invention therefore also relates to a copolymer derived from at least one monomer of the formula (I) and at least one ethylenically unsaturated comonomer which can undergo free radical copolymerization therewith.

Suitable comonomers are in principle all ethylenically unsaturated monomers which can undergo free radical polymerization with the monomers of the formula (I). Mixtures of a plurality of comonomers may also be used.

Examples of ethylenically unsaturated comonomers are alpha-olefins, aliphatic hydrocarbons having two or more conjugated double bonds, vinyl esters of saturated carboxylic acids, esters of ethylenically unsaturated mono- or dicarboxylic acid and/or alkenylaromatics.

Examples of alpha-olefins are monoethylenically unsaturated aliphatic hydrocarbons having two to ten carbon atoms, particularly preferably ethylene and propylene.

Examples of aliphatic hydrocarbons having two or more conjugated double bonds are dienes, in particular buta-1,3-diene.

Examples of vinyl esters of saturated carboxylic acids are vinyl esters of aliphatic saturated carboxylic acids having one to eighteen carbon atoms. These comonomers are described in more detail further below.

Examples of esters of ethylenically unsaturated mono- or dicarboxylic acids are alkyl esters of mono-ethylenically unsaturated $C_3$-$C_8$-mono- or dicarboxylic acids, in particular of acrylic acid, methacrylic acid, fumaric acid, maleic acid or itaconic acid. These comonomers are described in more detail further below.

Examples of alkenylaromatics are vinylaromatics, such as styrene or alpha-methylstyrene.

The preparation of the copolymers according to the invention can be effected by any desired types of free radical copolymerization.

Examples of these are mass polymerization, polymerization in solution, polymerization in suspension, in dispersion, in miniemulsion, in micro-emulsion or preferably polymerization in emulsion ("emulsion polymerization"). These polymerization types are known to the person skilled in the art.

The crosslinking monomer according to the invention can be used in the copolymerization as a bisulfite adduct containing an anion of the formula (I). The prepared bisulfite adduct can be used or the bisulfite adduct is prepared in situ in the polymerization mixture. Alternatively, however, a precursor monomer of the bisulfite adduct can also be used in the copolymerization, for example an aldehyde, and the copolymer formed can then be functionalized, for example by addition of bisulfite.

The crosslinking monomer of the formula (I) is generally used only in small amounts, for example in amounts of up to 10% by weight, based on the total amount of monomer, preferably in amounts of from 0.01 to 5% by weight.

The copolymers according to the invention are preferably copolymers containing structural units derived from ethylene, propylene, styrene, acrylate, methacrylate, vinyl esters of saturated carboxylic acids, butadiene or from mixtures of two or more of these monomers and containing up to 10% by weight of structural units, based on total monomer, which are derived from monomers of the formula (I).

Particularly preferred copolymers are present in the form of aqueous dispersions and are prepared by emulsion polymerization. The invention therefore also relates to compositions in the form of an aqueous dispersion containing a copolymer having structural units derived from monomers of the formula (I).

The preferred aqueous dispersions are substantially based on one or more ethylenically unsaturated compounds which are derived from vinyl esters and/or from esters of α,β-ethylenically unsaturated $C_3$-$C_8$-mono- or dicarboxylic acids and/or from alkenylaromatics, and from the monomers of the formula (I).

In principle, the following groups of monomers are suitable as a basis for the preferred aqueous dispersions:

One group comprises vinyl esters of monocarboxylic acids having one to eighteen carbon atoms, for example vinyl formate, vinyl acetate, vinyl propionate, vinyl isobutyrate, vinyl valerate, vinyl pivalate, vinyl-2-ethylhexanoate, vinyl decanoate, isopropenyl acetate, vinyl esters of saturated branched monocarboxylic acids having 5 to 15 carbon atoms in the acid radical, in particular vinyl esters of Versatic™ acids, vinyl esters of relatively long-chain saturated or unsaturated fatty acids, such as, for example, vinyl laurate, vinyl stearate, and vinyl esters of benzoic acid and substituted derivatives of benzoic acid, such as vinyl-p-tert-butyl benzoate. Among these, however, vinyl acetate is particularly preferred as a main monomer.

A further group of monomers which may be used in addition to the preferred vinyl esters and/or esters of α,β-ethylenically unsaturated $C_3$-$C_8$-mono- or dicarboxylic acids and/or the alkenylaromatics comprises aliphatic, monoolefinically or diolefinically unsaturated, optionally halogen-substituted hydrocarbons, such as ethene, propene, 1-butene, 2-butene, isobutene, conjugated $C_4$-$C_8$-dienes, such as 1,3-butadiene, isoprene, chloroprene, vinyl chloride, vinylidene chloride, vinyl fluoride or vinylidene fluoride.

A further group of monomers for the preferred aqueous dispersions comprises esters of α,β-ethylenically unsaturated $C_3$-$C_8$-mono- or dicarboxylic acids with preferably $C_1$-$C_{18}$-alkanols and in particular $C_1$-$C_8$-alkanols or $C_5$-$C_8$-cycloalkanols. The esters of the dicarboxylic acids may be monoesters or preferably diesters. Suitable $C_1$-$C_8$-alkanols are, for example, methanol, ethanol, n-propanol, isopropanol, 1-butanol, 2-butanol, isobutanol, tert-butanol, n-hexanol and 2-ethylhexanol. Suitable cycloalkanols are, for example, cyclopentanol or cyclohexanol. Examples are esters of acrylic acid, of methacrylic acid, of crotonic acid, of maleic acid, of itaconic acid, of citraconic acid or of fumaric acid, such as methyl(meth)acrylate, ethyl(meth)acrylate, isopropyl (meth)acrylate, n-butyl(meth)acrylate, isobutyl(meth)acrylate, 1-hexyl(meth)acrylate, tert-butyl(meth)acrylate, 2-ethylhexyl(meth)acrylate, di-n-methyl maleinate or fumarate, di-n-ethyl maleinate or fumarate, di-n-propyl maleinate or fumarate, di-n-butyl maleinate or fumarate, diisobutyl maleinate or fumarate, di-n-pentyl maleinate or fumarate, di-n-hexyl maleinate or fumarate, dicyclohexyl maleinate or fumarate, di-n-heptyl maleinate or fumarate, di-n-octyl maleinate or fumarate, di-(2-ethylhexyl)maleinate or fumarate, di-n-nonyl maleinate or fumarate, di-n-decyl maleinate or fumarate, di-n-undecyl maleinate or fumarate, dilauryl maleinate or fumarate, dimyristyl maleinate or fumarate, dipalmitoyl maleinate or fumarate, distearyl maleinate or fumarate and diphenyl maleinate or fumarate.

A further group of preferably used monomers comprises the alkenylaromatics. These are monoalkenylaromatics. Examples of these are styrene, vinyltoluene, vinylxylene, α-methylstyrene or o-chlorostyrene.

Said monomers are as a rule the main monomers, which together usually account for a proportion of more than 50% by weight, preferably more than 75% by weight, based on the total amount of the monomers to be polymerized by the free radical aqueous polymerization process.

The monomers should preferably be chosen so that a copolymer having adhesive, binder or coating properties forms. This can be effected by adjusting the glass transition temperature of the resulting polymers in a manner known per se.

Preferred main monomers are based on the following polymer classes.

Homo- or copolymers of one or more vinyl esters, in particular of vinyl acetate; copolymers of vinyl esters with esters of α,β-ethylenically unsaturated $C_3$-$C_8$-mono- or dicarboxylic acids with $C_1$-$C_8$-alkanols, in particular esters of (meth) acrylic acid and maleic acid or fumaric acid; copolymers of vinyl esters, in particular vinyl acetate, with ethene; terpolymers of vinyl esters, ethene and esters of α,β-ethylenically unsaturated $C_3$-$C_8$-mono- or dicarboxylic acids with $C_1$-$C_8$-alkanols, in particular esters of (meth)acrylic acid and maleic acid or fumaric acid; homo- or copolymers of esters of (meth) acrylic acid; copolymers of styrene with butadiene and/or esters of α,β-ethylenically unsaturated $C_3$-$C_8$-mono- or dicarboxylic acids with $C_1$-$C_8$-alkanols, in particular esters of (meth)acrylic acid.

Of course, further comonomers which modify the properties in a targeted manner can be concomitantly used in the polymerization. Such auxiliary monomers are usually incorporated in the form of polymerized units only as modifying monomers in amounts, based on the total amount of the monomers to be polymerized, of less than 50% by weight, as a rule of less than 20, preferably of less than 10, % by weight.

These monomers serve for further stabilization of the aqueous dispersions, can improve the film cohesion or other properties by crosslinking during the polymerization or during the film formation and/or react by a suitable functionality with formulation components with crosslinking.

Monomers which may serve for further stabilization are as a rule monomers which have an acid function and/or salts thereof. This group includes, for example, α,β-monoethylenically unsaturated mono- and dicarboxylic acids having 3 to 10 carbon atoms, ethylenically unsaturated sulfonic acids, ethylenically unsaturated phosphonic acids or dihydrogen phosphates and the water-soluble salts thereof, for example the sodium salts thereof. Preferred monomers from this group are vinylsulfonic acid and its alkali metal salts, acrylamidopropanesulfonic acid and its alkali metal salts, ethylenically unsaturated $C_3$-$C_8$-carboxylic acids and $C_4$-$C_8$-dicarboxylic acids, e.g. itaconic acid, crotonic acid, vinylacetic acid, acrylamidoglycolic acid and in particular acrylic acid and methacrylic acid.

Examples of further crosslinking auxiliary monomers are monomers having two or more vinyl radicals, monomers having two or more vinylidene radicals and monomers having two or more alkenyl radicals. The diesters of dihydric alcohols with α,β-monoethylenically unsaturated monocarboxylic acids, among which acrylic and methacrylic acid are preferred, the diesters of divalent carboxylic acids with ethylenically unsaturated alcohols, other hydrocarbons having two ethylenically unsaturated groups or the diamides of difunctional amines with α,β-monoethylenically unsaturated monocarboxylic acids are particularly advantageous.

Examples of such monomers having two nonconjugated ethylenically unsaturated double bonds are alkylene glycol diacrylates and dimethacrylates, such as ethylene glycol diacrylate, 1,2-propylene glycol diacrylate, 1,3-propylene glycol diacrylate, 1,3-butylene glycol diacrylate, 1,4-butylene glycol diacrylates or -methacrylates and ethylene glycol diacrylates or -methacrylates, 1,2-propylene glycol dimethacrylate, 1,3-propylene glycol dimethacrylate, 1,3-butylene glycol dimethacrylate, 1,4-butylene glycol dimethacrylates, hexanediol diacrylate, pentaerythrityl diacrylate, and divinylbenzene, vinyl methacrylate, vinyl acrylate, vinyl crotonate, allyl methacrylate, allyl acrylate, diallyl maleate, diallyl fumarate, diallyl phthalate, cyclopentadienyl acrylate, divinyl adipate or methylenebisacrylamide.

However, it is also possible to use monomers having more than two double bonds, for example tetraallyloxyethane, trimethylolpropane triacrylate or triallyl cyanurate.

A further group of auxiliary monomers is suitable for reaction with crosslinking under chosen conditions, either by self-crosslinking or crosslinking with a suitable monomeric reactant and/or with the structural units derived from monomers of the formula (V):

This group includes monomers having N-functional groups, including in particular (meth)acrylamide, allyl carbamate, acrylonitrile, methacrylonitrile, acryl-amidoglycolic acid, methyl acrylamidomethoxyacetate, N-(2,2-dimethoxy-1-hydroxyethyl)acrylamide, N-dimethyl-aminopropyl (meth)acrylamide, N-methyl(meth)acrylamide, N-butyl (meth)acrylamide, N-cyclohexyl(meth)acrylamide, N-dodecyl(meth)acrylamide, N-benzyl(meth)acrylamide, p-hydroxyphenyl(meth)acrylamide, N-(3-hydroxy-2,2-dimethylpropyl)methacrylamide, ethylimidazolidone (meth)acrylate, N-(meth)acryloyloxyethylimidazolidin-1-one, N-(2-methacrylamidoethyl)imidazolin-2-one, N-[[3-allyloxy-2-hydroxypropyl]aminoethyl]imidazolin-2-one, N-vinylformamide, N-vinylpyrrolidone or N-vinylethylene-urea.

A further group of auxiliary monomers comprises hydroxy-functional monomers, such as $C_1$-$C_9$-hydroxyalkyl methacrylates and acrylates, such as n-hydroxyethyl, n-hydroxypropyl or n-hydroxybutyl acrylate and methacrylate and the adducts thereof with ethylene oxide or propylene oxide.

A further group of auxiliary monomers comprises those which are crosslinkable or self-crosslinking via carbonyl groups. Examples are diacetone acrylamide, allyl acetoacetate, vinyl acetoacetate and acetoacetoxyethyl acrylate or methacrylate.

A further group of auxiliary monomers consists of monomers containing silane groups, e.g. vinyltrialkoxy-silanes, such as vinyltrimethoxysilane, vinyltriethoxy-silane, alkylvinyldialkoxysilanes or (meth)acryloyloxy-alkyltrialkoxysilanes, e.g. (meth)acryloxyethyl-trimethoxysilane or (meth)acryloxypropyltrimethoxy-silane.

A further group of auxiliary monomers consists of monomers containing epoxy groups, such as, for example, allyl glycidyl ether, methacryloyl glycidyl ether, butadiene monoepoxides, 1,2-epoxy-5-hexene, 1,2-epoxy-7-octene, 1,2-epoxy-9-decene, 8-hydroxy-6,7-epoxy-1-octene, 8-acetoxy-6,7-epoxy-1-octene N-(2,3-epoxy)-propylacrylamide, N-(2,3-epoxy)propylmethacrylamide, 4-acrylamidophenyl glycidyl ether, 3-acrylamidophenyl glycidyl ether, 4-methacrylamidophenyl glycidyl ether, 3-methacryamidophenyl glycidyl ether, N-glycidyloxy-methylacrylamide, N-glycidyloxypropylmethacrylamide, N-glycidyloxyethylacrylamide, N-glycidyloxyethylmeth-acrylamide, N-glycidyloxypropylacrylamide, N-glycidyl-oxypropylmethacrylamide, N-glycidyloxybutylacrylamide, N-glycidyloxybutylmethacrylamide, 4-acrylamidomethyl-2,5-dimethylphenylglycidyl ether, 4-methacrylamido-methyl-2,5-dimethylphenyl glycidyl ether, acrylamido-propyldimethyl(2,3-epoxy)propylammonium chloride, methacrylamidopropyldimethyl(2,3-epoxy)propylammonium chloride and glycidyl methacrylate.

In addition to the copolymer, the aqueous dispersions preferred according to the invention preferably contain protective colloids. These are polymeric compounds which are present during the emulsion polymerization and stabilize the dispersion.

Suitable protective colloids are, for example, polyvinyl alcohols, polyalkylene glycols, alkali metal salts of polyacrylic acids and polymethacrylie acids, cellulose, starch and gelatin derivatives or polymers derived from acrylic acid, methacrylic acid, maleic acid, maleic anhydride, methyl vinyl ether, styrene, 2-acrylamido-2-methylpropanesulfonic acid and/or 4-styrenesulfonic acid and the alkali metal salts thereof, but also polymers derived from N-vinyl-pyrrolidone, N-vinylcaprolactam, N-vinylcarbazole, 1-vinylimidazole, 2-vinylimidazole, 2-vinylpyridine, 4-vinylpyridine, acrylamide, methacrylamide, amine group-carrying acrylates, methacrylates, acrylamides and/or methacrylamides. A detailed description of further suitable protective colloids is to be found in Houben-Weyl, Methoden der organischen Chemie, Vol. XIV/1, Makromolekulare Stoffe [Macromolecular Compounds], Georg-Thieme-Verlag, Stuttgart, 1961, pages 411 to 420.

If the protective colloids are polyvinyl alcohol, in particular polyvinyl alcohol having a degree of hydrolysis of 60-100 mol %, preferably from 70 to 98 mol %, and viscosities of the 4% strength by weight aqueous solution at 20° C. of from 2 to 70 mPa·s or mixtures of these types is or are used. In addition to "homopolymeric" polyvinyl alcohol, i.e. polyvinyl alcohol consisting only of vinyl alcohol and residual vinyl acetate groups, copolymeric or functionalized polyvinyl alcohols can be used, for example reaction products of polyvinyl alcohol with diketene or with polyvinyl alcohol types carrying carboxyl groups, thiol groups, formamido groups, amino groups, arylamino groups, sulfate groups, sulfonate groups, phosphonate groups, quaternary ammonium groups and other functional groups.

Protective colloids which can form complexes or coordinate bonds with a group of compounds selected from the group consisting of the acidic metal salts or salts or acids of oxo anions, in particular aluminum chloride, aluminum nitrate, titanium sulfate or zirconium oxychloride, or phosphoric acid or boric acid are particularly preferably used in the aqueous dispersions.

Said polymeric stabilizers can be added to the aqueous dispersions optionally also during or after the polymerization.

Based on the solids content of the aqueous dispersions, the proportion of the polymeric protective colloids is preferably from 1 to 35% by weight, in particular from 2 to 20% by weight.

In addition to or instead of the protective colloids, the aqueous dispersion may also be stabilized with emulsifiers. These may be ionic, preferably anionic, or in particular nonionic, wetting agents. A list of suitable emulsifiers is to be found in Houben-Weyl, Methoden der organischen Chemie, Vol. XIV/I, Makromolekulare Stoffe, Georg-Thieme-Verlag, Stuttgart, 1961, pages 192-208.

The proportion of the emulsifiers may be up to 10% by weight, based on the solids content of the aqueous dispersion. Emulsifiers may already be present during the polymerization and/or may be added thereafter.

Aqueous dispersions which contain protective colloids and possibly up to 2% by weight, based on the solids content of the polymer dispersion, of ionic and/or nonionic emulsifiers are preferred.

The polymer and/or the protective colloid and/or the emulsifier may have groups crosslinkable with aldehydes. These are, for example, activated methylene groups, amino, amido, ureido and in particular hydroxyl groups.

Aqueous dispersions which have protective colloids with hydroxyl groups, in particular polyvinyl alcohol and alkylated celluloses, are particularly preferably used.

The aqueous dispersions according to the invention may contain further customary additives. These include, for example, film formation auxiliaries for depressing the minimum film formation temperature ("MFT depressives"), plasticizers, buffers, pH adjusters, dispersants, antifoams, fillers, dyes, pigments, silane coupling agents, thickeners, viscosity regulators, solvents and/or preservatives.

One group of additives comprises external crosslinking agents, which may be present in low molecular weight form or as crosslinking resins. These may even further improve the effect of the improvement of the water resistance in combination with the crosslinking agent according to the invention and are therefore particularly preferably used in the compositions according to the invention.

Suitable external crosslinking agents are, for example, phenol-formaldehyde resins, resorcinol-formaldehyde resins, melamine-formaldehyde resins, hydroxymethyl-substituted imidazolidinones or thioimidazolidinones, hydroxymethyl-substituted pyrimidinones or hydroxy-methyl-substituted triazinones or glycolurils or self-condensation products thereof or mixed condensates of two or more of said compounds, or a mixture of two or more of said compounds. 1,3-bis(Hydroxymethyl)-4-methoxy-4,5,5-trimethyl-2-imidazolidinone, N,N'-dimethylol-4-methoxy-5,5-dimethylpropyleneurea, N,N',N'',N'''-tetrakis(hydroxymethyl)glycoluril, 4,5-dihydroxy-1,3-bis(methoxymethyl)-2-imidazolidinone, 4,5-dihydroxy-1,3-bis(hydroxymethyl)imidazolidln-2-one, tetrahydro-1,3-bis(hydroxymethyl)-4-methoxy-5,5-dimethylpyrimidin-2(1H)-one, 4,5-dihydroxy-1,3-dimethylol-2-imidazolidinone, 4,5-dihydroxy-1,3-dimethyl-2-imidazolidinone, tetrahydro-1,3-bis(hydroxymethyl)-4-hydroxy-5,5-dimethyl-(1H)-pyrimidin-2-one, (=1,3-dimethylol-4-methoxy-5,5-dimethylpropyleneurea), tetrahydro-1,3-bis(hydroxymethyl)-4-alkoxy-5,5-dimethyl-(1H)-pyrimidin-2- one and N,N',N'',N'''-tetrakis(hydroxy-methyl)glycoluril may be mentioned by way of example for this purpose. The partly or completely etherified resins mentioned in EP-A 1 505 085 and based on methylolated ethylene ureas, propylene ureas, glyoxyldiureas, malondialdehydediureas or combinations thereof are likewise preferred. Among these external crosslinking agents, those which have no hydroxymethyl groups and therefore no formaldehyde source are particularly preferably used.

A further outstandingly suitable group of additives comprises other polyaldehydes, such as dialdehyde starches or other water-soluble polyaldehydes, and likewise the at least partly masked polyaldehydes of EP-A-686,682. These compounds, in combination, with the copolymers modified according to the invention, can contribute to a higher crosslinking density.

A further outstandingly suitable group of additives comprises polyhydrazine derivatives, in particular the compounds mentioned in EP-A-3,516.

Compositions additionally containing at least partly masked polyaldehydes or polyhydrazine derivatives are particularly preferred.

The aqueous dispersion according to the invention preferably has a pH suitable for eliminating the bisulfite group. These may be systems which have been rendered acidic or basic. In one embodiment, the compositions according to the invention have an acidic pH. This pH range is preferably from 2 to 6, in particular from 2.5 to 4.5. A suitable pH may already be reached after the emulsion polymerization for the preparation of the aqueous dispersion or can be established subsequently by adding acidic compounds. In order to establish the pH in the desired acidic range, organic or inorganic Lewis and Brønsted acids are suitable. Preferred Brønsted acids have a $pK_a$ of <2.5, for example hydrochloric acid, sulfuric acid, nitric acid, perchloric acid, p-toluenesulfonic acid, in particular phosphoric acid. Particularly suitable Lewis acids are the acidic salts of complexable metal ions, in particular aluminum chloride, aluminum nitrate, zirconium oxychloride and titanium sulfate, in particular the acidic salts having polyvalent complexable cations, as mentioned, for example, in DE-B 22 61 402, DE-C 26 20 738 and DE-A 39 42 628.

This group of products consisting of the pH adjusters is preferably simultaneously capable of forming coordinate bonds or of complex formation with the protective colloids of the aqueous dispersions. In particular, the acidic salts of complexable metal ions, in particular aluminum chloride, aluminum nitrate, zirconium oxychloride and titanium sulfate, in particular the acidic salts having polyvalent complexable cations, as mentioned, for example, in DE-B 22 61 402, DE-C 26 20 738 and DE-A 39 42 628, are suitable for this purpose.

Aqueous dispersions having a pH of from 2 to 6, in particular from 2.5 to 4.5, are therefore preferred.

The solids content of the aqueous dispersions according to the invention is preferably from 20 to 70% by weight, in particular from 30 to 65% by weight.

The preparation of the aqueous dispersions can be effected by the customary continuous or batchwise free radical polymerization procedures.

The performance of a free radical aqueous emulsion polymerization of ethylenically unsaturated monomers has often been described in the past and is therefore sufficiently well known to the person skilled in the art (cf. for example, Encyclopedia of Polymer Science and Engineering, Vol. 8, pages 659 to 677, John Wiley & Sons, Inc., 1987; D. C. Blackley, Emulsion Polymerisation, pages 155 to 465, Applied Science Publishers, Ltd., Essex, 1975; D. C. Blackley, Polymer Latices, 2nd Edition, Vol. I, pages 33 to 415, Chapman & Hall, 1997; H. Warson, The Applications of Synthetic Resin Emulsions, pages 49 to 244, Ernest Bonn Ltd., London, 1972; D. Diederich, Chemie in unserer Zeit 1990, 24, pages 135 to 142, Verlag Chemie, Weinheim; J. Piirma, Emulsion Polymerisation, pages 1 to 287, Academic Press, 1982; F. Hölscher, Dispersionen synthetischer Hochpolymerer [Dispersions of Synthetic High Polymers], pages 1 to 160, Springer-Verlag, Berlin, 1969, and the patent DE-A 40 03 422). It is usually effected in such a way that the ethylenically unsaturated monomers are dispersed in an aqueous medium, frequently with the concomitant use of dispersants, and are polymerized by means of at least one free radical polymerization initiator.

Water-soluble and/or oil-soluble initiator systems, such as peroxodisulfates, azo compounds, hydrogen peroxide, organic hydroperoxides or dibenzoyl peroxide, are used here. These may be used either by themselves or in combination with reducing compounds, such as Fe(II) salts, sodium pyrosulfite, sodium hydrogen sulfite, sodium sulfite, sodium dithionite, sodium formaldehyde sulfoxylate, ascorbic acid, as a redox catalyst system.

The polymeric protective colloids and/or emulsifiers can be added before or during the polymerization. An additional subsequent addition of polymeric stabilizers and/or of emulsifiers is likewise possible. Additives intended for the desired application are then optionally added to this dispersion.

The formulation of the aqueous dispersions preferred according to the invention can be effected in the apparatuses known for this purpose to the person skilled in the art, for example in stirred tanks or suitable mixers. Mixing of different components only shortly before the application by means of, for example, inline spray guns or similar devices, is likewise possible.

The copolymer compositions according to the invention can be processed to give products having very high water resistance without having to accept a risk of formaldehyde formation.

The copolymers according to the invention, in particular in the form of aqueous dispersions, are used, for example, as binders in preparations which serve for the coating of substrates of all kinds. These include, for example, synthetic resin-bound renders, tile adhesives, sealing compounds and surface sealants, preferably for porous components, and paper coating slips, paints, such as, for example, emulsion paints, emulsion finishes and glazes, and binders for nonwovens, glass fibers and fiberfill.

The copolymers according to the invention, in particular in the form of aqueous dispersions, are particularly preferably used as adhesives for adhesive bonding of any desired substrates.

The present invention likewise relates to these uses.

The copolymers according to the invention, in particular in the form of aqueous dispersions, are particularly preferably used for adhesive bonding of porous or semiporous substrates or as a binder for porous and semiporous substrates.

The copolymers according to the invention, in particular in the form of aqueous dispersions, are specifically suitable for use as water-resistant adhesive, in particular for cellulosic substrates, such as wood, in particular solid wood, or materials and engineering materials derived from wood, for example veneers, plywood, laminated wood, layered wood, densified laminated wood, composite boards or wood fiber materials, such as porous, permeable, hard or medium density wood fiber boards (MDF) or plastic-coated decorative wood fiber boards. The copolymers are suitable for manual or mechanical application and in particular also for applications in which the adhesive joints are hardened by high frequency alternating currents.

Further general examples of use are water-resistant adhesive bonding of paper, board, corrugated board, foam, cement, leather, textile or densified laminated materials.

Other applications are in adhesives for the construction sector, as floor, wall or ceiling adhesive, or as furniture film adhesive or carpet backing adhesive.

Further areas of suitability are in water-resistant binders for wood fiber boards or fibrous leather and binders for insulating materials comprising paper fibers or plastics fibers, and furthermore in water-resistant construction material dispersions as a binder for render or cement.

A further field of use for the copolymers according to the invention, in particular in the form of aqueous dispersions, comprises binders for textile and nonwoven (so-called engineered fabrics) and in textile printing and as a textile finish.

A preferred field of use consists in the use as a binder for glass fibers which are used, for example, for strengthening plastics tiles, moldings and as insulating material, or as a binder for ceramic.

A further preferred field of use consists in the use as a binder for paints, in particular for emulsion paints, emulsion finishes and glazes.

The compositions according to the invention can also be used for producing redispersible dispersion powders. These can be produced in a manner known per se by spraying the aqueous dispersions.

The following examples serve for illustrating the invention. The parts and percentages stated in the examples are based on weight, unless noted otherwise.

EXAMPLE 1A

Preparation of 2-formylethyl acrylate on the Basis of JP-A-60/72,954

159.6 g (2.85 mol) of acrolein (quality >95%, Fluka) were initially introduced together with 100 mg of hydroquinone in a cylindrical glass reactor having a capacity of 3000 ml and provided with a stirrer and metering apparatuses. Thereafter, 1024 g (14.2 mol) of acrylic acid (BASF AG) and then 66.6 g of Amberlyst A (basic ion exchanger from Rohm & Haas) were added with stirring. The mixture was heated to an internal temperature of 50° C. in a water bath, stirred at this temperature for 10 hours and then cooled to room temperature. For isolating the crude product, the cooled reaction mixture was filtered over a fluted filter and the filtrate was evaporated in a rotary evaporator under a water jet vacuum at a bath temperature of 72° C. until no more distillate passed over. The residue of evaporation was taken up in 400 ml of dichloromethane and stirred rapidly 8 times with 400 ml of 5% strength sodium bicarbonate solution each time in a beaker and then shaken with 2 times 400 ml of deionized water. The organic phase was dried over 20 g of magnesium sulfate and the methylene chloride was then evaporated off in a rotary evaporator. The residue (35.8 g) was distilled in vacuo. The main fraction was obtained at the boiling range of 79-81° C. (P<2 mm Hg). Yield: 12 g (3.3%, based on acrolein used).

The IR spectrum of the compound was identical to the spectrum published in JP-A-60/72,954, on page 4.

EXAMPLE 1B

Preparation of the Bisulfite Adduct of 2-formylethyl acrylate (FEA-BSA)

12 g (0.094 mol) of 2-formylethyl acrylate were initially introduced into a 100 ml conical flask blanketed with nitrogen, and 0.076 g (0.5 mmol) of 1-phenyl-3-pyrazolidinone (as a stabilizer) was added. Thereafter, a solution of 5.34 g (0.028 mol) of sodium metabisulfite in 117 ml of deionized water were added dropwise to the reaction mixture with thorough mixing and cooling with water (about 20° C.) over 15 minutes. After the end of the addition, stirring was effected for a further 10 minutes. Thereafter, the reaction mixture was extracted with 2× about 30 ml of ethyl acetate for recovering unconverted 2-formylethyl acrylate (see below). For precipitating the adduct, 12 ml of ethanol were first added to the aqueous phase in an ice bath and stirring was effected until the product was precipitated. Thereafter, about 30 ml of ethyl acetate cooled in an ice bath were added to the reaction mixture and the finely crystalline precipitate was suspended. The product was filtered over a suction filter, washed with the remaining ethyl acetate and dried in a vacuum drying oven. 5.2 g (22.5%), based on aldehyde used, were obtained.

$^1$H-NMR (D$_2$O; RT; ppm: 6.45 H$_{cis}$H$_{trans}$C=CH— (dd, J=17.4 1.1 Hz, 1H), 6.22 H$_{cis}$H$_{trans}$C=CH— (dd, J=17.4, 10.6 Hz, 1H), 6.00 H$_{cis}$H$_{trans}$C=CH— (dd, J=10.6, 1.1 Hz, 1H), 4.56 HO—C(H)SO$_3$Na— (m, 1H), 4.38 —O—CH$_2$— (m, 2H), 2.38, 2.05 —CH$_{A/B}$—C(H)(OH)SO$_3^-$ (m, 1H; m 1H).

$^{13}$H-NMR (D$_2$O; RT; ppm): 171.1 —C(=O)—O—, 135.3 H$_2$C=, 130.2 =CH—, 83.5 —C(H)(OH)—SO$_3^-$, 64.2 —O—CH$_2$—, 32.9 —CH$_2$—C(H)(OH)SO$_3^-$ IR (KBr, cm$^{-1}$): 3416 br. s, 2964 w, 1726 s, 1636 m, 1619 w, 1412 m, 1299 m, 1199 s, 1123 m, 1044 s, 987 m, 812 m, 635 m, 585 m, 536 m, 436 w.

EXAMPLE 2A

Preparation of 3-formylpropyl acrylate by Oxidation of Butanediol Monoacrylate

The reaction described below was carried out on the basis of P. L. Anelli, F. Montanari, S. Quici; Organic Syntheses, Coll. Vol. 8, 367 (1993); Vol. 69, 212 (1990).

96.1 g (0.667 mol) of butanediol monoacrylate (commercial product of BASF AG) and 1.17 g (7.51 mmol) of TEMPO (2,2,6,6-tetramethylpiperidin-N-oxyl) were weighed into a 2 l three-necked round-bottomed flask with magnetic stirrer and internal thermometer and dissolved in 340 g of methylene chloride. A solution of 8.94 g (75.1 mmol) of KBr in 37.5 ml of deionized water was added thereto and cooled to 0-10° C. by means of a suitable, effective cooling apparatus with thorough mixing. In a separate vessel, 614 g (about 0.825 mol) of an aqueous approx. 10% strength sodium hypochlorite solution were diluted with 200 ml of deionized water and adjusted to pH 9 with 25.5 g (0.304 mol) of sodium bicarbonate (the pH should be checked using a suitable measuring apparatus; required amount of sodium bicarbonate may differ depending on the sodium hypochlorite solution used) and then added dropwise to the reaction mixture via a dropping funnel in the course of 15-20 minutes. The temperature was kept as far as possible (cooling) just above 0° C. and was not to exceed 15° C. After addition was complete, stirring was effected for a further 3 minutes. After the end of the reaction, the organic phase and the aqueous phase were separated from one another as rapidly as possible and the aqueous phase was extracted with 260 g of methylene chloride. The combined organic phases were then washed in succession with a solution of 2.40 g (14.5 mmol) of potassium iodide in 150 ml of 10% strength aqueous hydrochloric acid, a solution of 9.9 g (62.6 mmol) of sodium thiosulfate in 90 ml of water, 2×150 ml of a 10% strength sodium bicarbonate solution in deionized water and finally with 150 ml of deionized water. The organic phase was dried over anhydrous magnesium sulfate and the solvent was then removed in a rotary evaporator. 89 g of crude product were obtained. About 6 mol % of butanediol monoacrylate and about 1 mol % of a hemiacetal of 3-formylpropyl acrylate and butanediol monoacrylate were still present as main impurities in the crude product. The crude product can, however, be used without further purification for the preparation of the bisulfite adduct.

$^1$H-NMR (CDCl$_3$; RT; ppm): 9.80 —CH═O (t, J=1.2 Hz, 1H), 6.39 H$_{cis}$H$_{trans}$C═CH— (dd, J=17.5, 1.5 Hz, 1H), 6.11 H$_{cis}$H$_{trans}$C═CH— (dd, J=17.5, 10.5 Hz, 1H), 5.84 H$_{cis}$H$_{trans}$C═CH— (dd, J=10.5, 1.5 Hz, 1H), 4.20 —O—CH$_2$— (t, J=6.5 Hz, 2H), 2.57 —CH$_2$—CH═O (td, J=7.0, 1.2 Hz, 2H), 2.03 —CH$_2$—CH$_2$—CH$_2$— (tt, J=7.0, 6.5 Hz, 2H).

$^{13}$H-NMR (CDCl$_3$; RT; ppm): 201.1 —CH═O, 166.0 —C(═O)—O—, 130.9 H$_2$C═, 128.3 ═CH—, 63.5 —O—CH$_2$—, 40.5 —CH$_2$—CH═O, 21.4 —CH$_2$—CH$_2$—CH$_2$—.

IR (film on KBr, cm$^{-1}$): 3107 w, 3039 w, 2962 m, 2900 m, 2832 m, 2728 m, 1724 s, 1636 m, 1620 m, 1457 m, 1442 m, 1410 s, 1297 s, 1273 s, 1192 s, 1063 s, 986 s, 811 s, 667 w.

EXAMPLE 2B

Bisulfite Adduct of 3-formylpropyl acrylate (FPA-BSA)

133 g (0.93 mol) of 3-formylpropyl acrylate were initially introduced into a 250 ml 2-necked flask blanketed with nitrogen, and 0.76 g (4.7 mmol) of 1-phenyl-3-pyrazolidinone (as a stabilizer) was added. Thereafter, a solution of 53.2 g (0.28 mol) of sodium metabisulfite in 117 ml of deionized water was added dropwise to the reaction mixture with thorough mixing and cooling with water (about 20° C.) over 15 minutes. After the end of the addition, stirring was effected for a further 10 minutes. Thereafter, the reaction mixture was extracted with 2× approx. 100 ml of ethyl acetate for recovering unconverted 3-formylpropyl acrylate (see below). Thereafter, 100 ml of ethanol were added to the aqueous phase in an ice bath and stirred until the product crystallized. Thereafter, about 500 ml of precooled ethyl acetate were added to the crystal slurry likewise in the ice bath and a suspension was produced and then filtered. The filtercake comprising 3-formylpropyl acrylate was washed with 2×300 ml of ethyl acetate and dried. 82 g (36%, based on aldehyde; 60%, based on sodium metabisulfite) were obtained.

For recovering unconverted 3-formylpropyl acrylate, the ethyl acetate phase was dried over anhydrous magnesium sulfate and the methylene chloride was removed in vacuo. The recycled material still contained unknown impurities but could be used without problems as a 50/50 mixture with fresh aldehyde for the preparation of the bisulfite adduct of 3-formylpropyl acrylate.

$^1$H-NMR (d6-DMSO; RT; ppm): 6.32 H$_{cis}$H$_{trans}$C═CH— (dd, J=17.3, 1.6 Hz, 1H), 6.17 H$_{cis}$H$_{trans}$C═CH— (dd, J=17.3, 10.3 Hz, 1H), 5.93 H$_{cis}$H$_{trans}$C═CH— (dd, J=10.3, 1.6 Hz, 1H), 5.23 HO—C(H)SO$_3^-$ (d, J=5.7 Hz, 1H), 4.10 —O—CH$_2$— (m, 2H), 3.82 HO—C(H)SO$_3$Na— (M, 1h), 1.80 —CH$_2$—CH$_2$—CH$_2$— (m, 2H), 1.65, 1.52 —CH$_{A/B}$—C(H)(OH)SO$_3$ (m, 1H; m 1H).

$^{13}$H-NMR (d6-DMSO; RT; ppM): 169.3 —C(═O)—O—, 131.3 H$_2$C═ 128.3 ═CH—, 82.3 —C(H)(OH)—SO$_3^-$, 64.1 —O—CH$_2$—, 28.0/24.8 —CH$_2$—CH$_2$—C(H)(OH)SO$_3^-$

IR (KNr, cm$^{-1}$): 3352 br. s, 3040 w, 2960 m, 2902 w, 1729 s, 1634 m, 1620 w, 1467 m, 1409 m, 1390 m, 1362 m, 1296 s, 1272 s, 1246 s, 1230 s, 1212 s, 1189 s, 1168 s, 1151 s, 1122 m, 1098 m, 1046 s, 986 s, 885 w, 809 m, 765 w, 675 m, 632 s.

Polymerizations with the Bisulfite Adducts FEA-BSA and FPA-BSA

All stated amounts in "parts" are understood as meaning mass of the respective substance, based on the mass of the vinyl acetate used.

General method: A solution of 10 parts of partly hydrolyzed polyvinyl alcohol having a degree of hydrolysis of 88 mol % and a viscosity of the 4% strength by weight solution at 20° C. of 18 mPa·s in 88 parts by weight of deionized water was prepared in a stirred glass tank reactor provided with anchor stirrer, feed facilities, reflux condenser, and jacketed against cooling. After addition of 0.09 part of ®Agitan 280 antifoam (Münzing-Chemie) and 0.1 part of sodium acetate, 8.8 parts of altogether 100 parts of vinyl acetate were incorporated by emulsification. The internal temperature was increased to 60° C. and the polymerization was initiated by addition of a solution of 0.02 part of ammonium persulfate in 0.66 part of deionized water.

After the reaction had started, 91.2 parts of vinyl acetate, a solution of 0.03 part of ammonium persulfate in 2.5 parts of deionized water and a solution of the functional comonomers mentioned in table 1 in 2.5 parts of deionized water were metered uniformly into the polymerization batch in three separate feeds in the course of three hours. The jacket temperature was controlled so that the polymerization took place at a slowly increasing internal temperature from 68° C. at the beginning to about 80° C. at the end of the metering.

After the end of the metering, a solution of 0.01 part of ammonium persulfate in 0.5 part of deionized water was added and postpolymerization was effected for initially one hour at 80° C.

In the case of examples 3 and C1, postpolymerization was effected with solutions of 0.04 part of Trigonox AW 70 (from Akzo, tert-butyl hydroperoxide) in 0.15 part of water and 0.07 part of ascorbic acid in 0.5 part of water at 80° C. and 75° C., respectively, for demonomerization. In examples 4-7, the demonomerization was effected with solutions of 0.08 part of sodium metabisulfite in 0.5 part of deionized water and 0.05 part of ammonium persulfate in 0.5 part of deionized water at 80° C./75° C. In these examples, in each case solutions of 0.2 part of sodium metabisulfite in 2 parts of deionized water were additionally stirred in for stabilization at room temperature. Dispersions having solids contents of from 51 to 53% were thus obtained. The viscosities of the products obtained are shown in table 2.

For testing as a wood adhesive, the products were modified with in each case 2 parts of butyldiglycol acetate, 0.025 part of ®Agitan 305 antifoam (Münzing-Chemie) and 5 parts of weight of a 28% strength aqueous aluminium chloride solution.

The testing of the formulated dispersions was effected on beech wood test specimens according to the test standard DIN EN 204/D3. In this test, the resistance of the adhesive film to exposure to cold water for four days is tested. Without use of crosslinking monomers, the adhesive film would have no water resistance at all, i.e. the test specimens would disintegrate during the storage. In addition to the basic information about the suitability of the products for use in the chosen application, the test also simultaneously provides information about the crosslinking density in the film, since the values of the wet adhesive strength decrease with increasing film swelling and reemulsifiability, which are effectively reduced by crosslinking. This is also evident from the water absorptions of the pure films, which were determined by a customary method (see EP-A 1 458 774, page 8). The gluing and testing were carried out taking into account the following characteristic data

TABLE 1

| Parameters of standard adhesive bond | |
|---|---|
| Glue application | 150 ± 20 g/m² (application on both sides) |
| Press time | 2 hours |
| Press pressure | 0.7 N/mm² |
| Number of test specimens per test sequence | 20 |
| Testing according to storage sequence in DIN EN 204 D3/3; immediate test | 7 days under standard climatic conditions 4 days in cold water |
| Test temperature | 23 ± 2° C. |
| Feed rate | 50 mm/min |
| Required tensile strength | ≥2 N/mm² |

Table 2 shows the results of the polymerizations and the results of the testing of the performance characteristics. In the case of comparative example C1, a polymerization with the customary crosslinking monomer N-methyiolacrylamide was carried out for comparison. For this purpose, a commercially available 48% strength product from S. N. F. Floerger was used. The amount stated in the table is based on the active substance. In examples 3 and 4, amounts of the bisulfite adduct monomers which are the molar equivalent of this amount were used in order to be able to make a direct comparison of the crosslinking efficiency. All formulations of the example dispersions according to the invention gave a non-reemulsifying film. The crosslinking effect observed is sufficient for safely complying with the chosen test standard. It can be seen that, in the case of equimolar replacement of N-methylolacrylamide by the novel monomers, the efficiency is comparable or, as in the case of FPA-BSA, is even better. Formaldehyde is neither introduced by the products nor forms during the crosslinking.

TABLE 2

| | | | | | |
|---|---|---|---|---|---|
| | | | Data from the polymerization experiments and tests | | |
| Example | Crosslinking monomer | Amount used (based on 100 parts of vinyl acetate) | Viscosity Brookfield RVT, 23° C. [mPa · s] | Water absorption of the film [%] after formulation | Wet adhesive strength on beech wood according to EN 204 D3/3 [N/mm²] after formulation |
| 3 | FEA-BSA | 0.88 | 11 600 | 27 | 2.6 |
| 4 | FPA-BSA | 0.93 | 120 000 | 14 | 7.0 |
| 5 | FPA-BSA | 0.7 | 41 000 | 22 | 3.9 |
| 6 | FPA-BSA | 0.47 | 26 400 | 32 | 2.6 |
| 7 | FPA-BSA | 0.23 | 19 950 | 35 | 1.5 |
| C1 | NMA | 0.38 | 28 750 | — | 2.3 |

The invention claimed is:

1. A compound in acid or salt form, which contains an anion of the formula (I) and one or more cations for producing electroneutrality

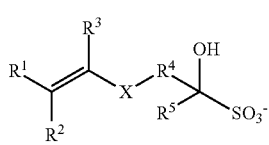

(I)

in which:

$R^1$ and $R^2$, independently of one another, are hydrogen, alkyl, cycloalkyl, aryl, aralkyl, —COOR⁵, —COO⁻ Cat⁺, —CON(R⁶R⁷) or —X—R⁴—CR⁵ (OH)(SO₃⁻);

$R^4$ is alkylene, polyoxyalkylene, cycloalkylene or arylene;

$R^5$ is hydrogen, alkyl, cycloalkyl or aryl;

$R^3$, $R^6$ and $R^7$, independently of one another, are hydrogen, alkyl or aryl:

Cat⁺ is a monovalent cation;

X is selected from the group consisting of —O—, —CH₂—O—, —COO— or —CONR⁸—; and $R^8$ is hydrogen, alkyl or aryl.

2. The compound as claimed in claim 1, wherein $R^1$ and $R^2$, independently of one another, are hydrogen, alkyl, —COOR⁵ or —COO⁻ Cat⁺, and wherein $R^3$ is hydrogen or alkyl.

3. The compound as claimed in claim 2, wherein one of the radicals $R^1$ or $R^2$ is —COOR⁵ or —COO⁻ Cat⁺.

4. The compound as claimed in claim 3, wherein $R^1$ and $R^2$, independently of one another, are hydrogen, methyl, —COOR⁵ᵃ or —COO⁻ Cat+ and wherein at least one of the radicals $R^1$ or $R^2$ is —COOR⁵ᵃ or —COO⁻ Cat+, $R^{5a}$ being hydrogen or $C_1$-$C_6$-alkyl, and wherein $R^3$ is hydrogen or methyl.

5. The compound as claimed in claim 1, wherein one of the radicals $R^1$ or $R^2$ is an —X—R⁴—CR⁵ (OH)(SO₃⁻) group.

6. The compound as claimed in claim 1, wherein X is —COO—.

7. The compound as claimed in claim 1, wherein $R^4$ is alkylene or polyoxyalkylene.

8. The compound as claimed in claim 7, wherein $R^4$ is unsubstituted $C_1$-$C_6$-alkylene.

9. The compound as claimed in claim 8, wherein $R^4$ is unsubstituted $C_1$-$C_4$-alkylene.

10. The compound as claimed in claim 1, wherein $R^5$ is hydrogen or alkyl.

11. The compound as claimed in claim 1, wherein the cations for producing electroneutrality are selected from the group consisting of hydrogen, ammonium, or mono- to tetravalent metal ions.

12. The compound as claimed in claim 1, wherein the anion of formula (I) is an anion of the formula (IVa) or (IVb)

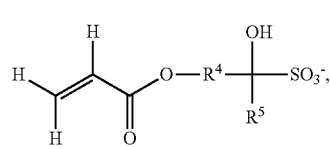

(IVa)

-continued

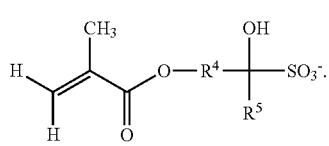
(IVb)

13. A compound in acid or salt form, which contains an anion of the formula (I) and one or more cations for producing electroneutrality

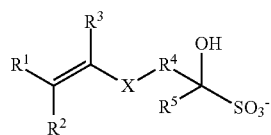
(I)

in which:

R$^1$ and R$^2$, independently of one another, are hydrogen, alkyl, cycloalkyl, aryl, aralkyl, —COOR$^5$, —COO$^-$Cat$^+$, —CON(R$^6$R$^7$), or —X—R$^4$—CR$^5$(OH)(SO$_3^-$), wherein at least one of the radicals R$^1$ or R$^2$ is —X—R$^4$—CR$^5$(OH)(SO$_3^-$);

R$^4$ is alkylene, polyoxyalkylene, cycloalkylene or arylene;

R$^5$ is hydrogen, alkyl, cycloalkyl or aryl;

R$^3$, R$^6$ and R$^7$, independently of one another, are hydrogen, alkyl or aryl;

Cat$^+$ is a monovalent cation;

X is selected from the group consisting of —O—, —CH$_2$—O—, —CH$_2$—NR$^8$—, —COO— or —CONR$^8$—; and R$^8$ is hydrogen, alkyl or aryl.

14. A compound in acid or salt form, which contains an anion of the formula (IVa) or (IVb) and one or more cations for producing electroneutrality

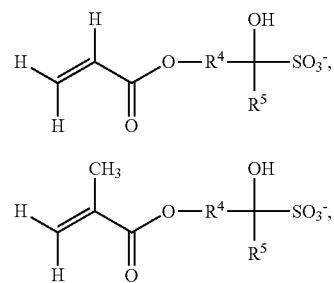

in which:

R$^4$ is alkylene, polyoxyalkylene, cycloalkylene or arylene; and

R$^5$ is hydrogen, alkyl, cycloalkyl or aryl.

* * * * *